(12) United States Patent
Jang et al.

(10) Patent No.: US 9,113,792 B2
(45) Date of Patent: Aug. 25, 2015

(54) METHOD AND APPARATUS FOR FORMING X-RAY MAMMOGRAM

(71) Applicant: SAMSUNG ELECTRONICS CO., LTD., Suwon-si (KR)

(72) Inventors: Kwang Eun Jang, Busan (KP); Jong Ha Lee, Hwaseong-si (KR); Young Hun Sung, Hwaseong-si (KR); Kang Eui Lee, Seoul (KR); Jae Hak Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 243 days.

(21) Appl. No.: 13/940,683

(22) Filed: Jul. 12, 2013

(65) Prior Publication Data

US 2014/0072100 A1    Mar. 13, 2014

(30) Foreign Application Priority Data

Sep. 7, 2012    (KR) .................... 10-2012-0099442

(51) Int. Cl.
*A61B 6/02* (2006.01)
*G06K 9/46* (2006.01)
(Continued)

(52) U.S. Cl.
CPC ................. *A61B 6/022* (2013.01); *A61B 6/025* (2013.01); *A61B 6/0414* (2013.01); *A61B 6/502* (2013.01);
(Continued)

(58) Field of Classification Search
CPC ............ A61B 6/00; A61B 6/025; A61B 6/03; A61B 6/4291; A61B 6/48; A61B 6/488; A61B 6/50; A61B 6/502; A61B 6/52; A61B 6/5211; A61B 6/5252; A61B 6/5258; G06T 1/00; G06T 1/0007; G06T 5/00; G06T 5/004; G06T 5/50; G06T 7/00; G06T 7/0012; G06T 7/0014; G06T 7/0051; G06T 7/0065; G06T 7/0067; G06T 7/0075; G06T 7/0077; G06T 7/0079; G06T 7/0081; G06T 7/0097; G06T 11/00; G06T 11/003; G06T 11/006; G06T 15/00; G06T 15/08; G06K 9/46; G06K 9/4604; G06K 9/4642; G06K 9/4647; G06K 9/60; G06K 9/62; G06K 9/6201; G06K 9/6212; G06K 9/6217; G06K 9/6232; G06K 9/6288; G06K 9/629; G06K 9/78; G06K 9/80; G06K 2009/6213
USPC ........... 378/21–27, 37, 51, 54–56, 62, 91, 98, 378/98.8, 114–116, 162, 165, 204, 210, 378/901; 382/128, 131, 168–170, 254, 266, 382/275, 276, 285, 307, 308, 325
See application file for complete search history.

(56) References Cited

U.S. PATENT DOCUMENTS 7,218,766 B2    5/2007    Eberhard et al.
7,340,032 B2    3/2008    Besson
(Continued)

*Primary Examiner* — Anastasia Midkiff
(74) *Attorney, Agent, or Firm* — Sughrue Mion, PLLC

(57) ABSTRACT

An X-ray imaging method and apparatus are provided for forming an X-ray image having reduced noise and showing a clear boundary of a lesion region. The X-ray imaging method includes performing a first main shot which irradiates an object in a compressed state by using X-rays at least once to obtain a single two-dimensional image, performing a second main shot which irradiates the object by using X-rays at different positions to obtain a plurality of two-dimensional images, and forming a two-dimensional final image by removing a lesion region having a unclear boundary from each of the plurality of two-dimensional images and substituting a lesion region of the single two-dimensional image into an area which corresponds to the removed lesion region.

18 Claims, 10 Drawing Sheets

(51) Int. Cl.
  *G06K 9/78* (2006.01)
  *G06K 9/80* (2006.01)
  *A61B 6/00* (2006.01)
  *G06K 9/62* (2006.01)
  *A61B 6/04* (2006.01)
  *G06T 7/00* (2006.01)

(52) U.S. Cl.
  CPC ............. *A61B 6/5217* (2013.01); *A61B 6/5252* (2013.01); *G06K 9/629* (2013.01); *G06K 9/6217* (2013.01); *A61B 6/488* (2013.01); *A61B 6/5235* (2013.01); *G06K 9/46* (2013.01); *G06K 9/78* (2013.01); *G06K 9/80* (2013.01); *G06T 7/0065* (2013.01)

(56) References Cited

U.S. PATENT DOCUMENTS

| 7,522,755 | B2 * | 4/2009 | Li et al. | 382/128 |
| 7,840,046 | B2 * | 11/2010 | Jerebko et al. | 382/128 |
| 2008/0247509 | A1 * | 10/2008 | Kashiwagi | 378/54 |

* cited by examiner

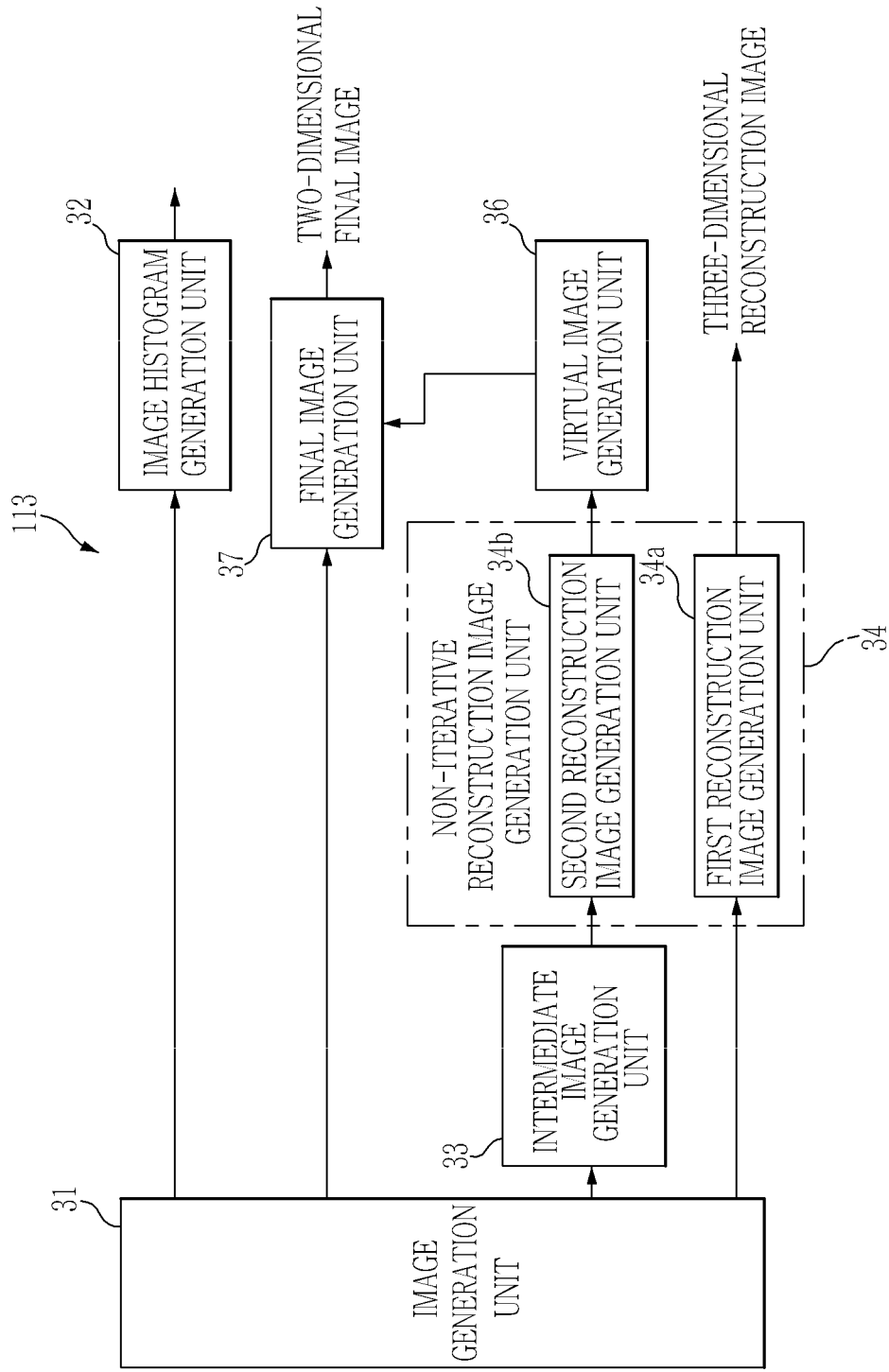

METHOD AND APPARATUS FOR FORMING X-RAY MAMMOGRAM

CROSS-REFERENCE TO RELATED APPLICATION

This application claims priority from Korean Patent Application No. 10-2012-0099442, filed on Sep. 7, 2012 in the Korean Intellectual Property Office, the disclosure of which is incorporated herein by reference in its entirety.

BACKGROUND

1. Field

Exemplary embodiments relate to an X-ray imaging method and apparatus for performing X-ray imaging by transmitting X-rays toward an object, reducing noise in soft tissue images of the object, and forming a clear X-ray image of a lesion region inside the object.

2. Description of the Related Art

Mammography uses radiation, such as X-rays, to capture an X-ray image of breasts, which image can then be used for diagnosing breast cancer. An apparatus using mammography may be, for example, a mammography system. The mammography system irradiates a breast with X-rays in a state in which the breast is compressed in order to obtain a two-dimensional X-ray image of the breast.

The mammography system is advantageous in that lesions inside breasts may be detected at low cost, and, in particular, a detection rate of microcalcifications is high. However, an image which is obtained using the mammography system is one slice of a two-dimensional X-ray image, and thus inner tissues of breasts overlap one another in the two-dimensional X-ray image. In particular, inner tissues of dense breasts overlap each other to a large extent, and thus it is difficult to distinguish normal tissues from lumps.

To address this problem of the mammography system, a tomosynthesis system has been developed. The tomosynthesis system performs radiography on a compressed breast at different angles while moving an X-ray generator which generates X-rays in order to obtain a three-dimensional X-ray image.

The tomosynthesis system performs radiography on a compressed breast at several angles and combines two-dimensional images which are obtained via the respective radiography processes in order to form a three-dimensional image. Thus, the tomosynthesis system may provide reduced overlapping of inner tissues of a breast as compared to the mammography system.

SUMMARY

One or more exemplary embodiments provide an X-ray imaging method and apparatus by which an X-ray image having reduced noise and showing a clear boundary of a lesion region may be obtained.

Additional aspects of the exemplary embodiments will be set forth in part in the description which follows and, in part, will be obvious from the description, or may be learned by practice of the exemplary embodiments.

In accordance with an aspect of an exemplary embodiment, there is provided an X-ray imaging method including performing a first main shot which irradiates an object in a compressed state by using X-rays at least once in order to obtain a single two-dimensional image, performing a second main shot which irradiates the object by using X-rays at different positions in order to obtain a plurality of two-dimensional images, and forming a two-dimensional final image by removing a lesion region having an unclear boundary from each of the plurality of two-dimensional images which are obtained by performing the second main shot and substituting a lesion region of the single two-dimensional image into an area which corresponds to the removed lesion region.

In accordance with an aspect of another exemplary embodiment, there is provided an X-ray imaging apparatus including an X-ray generator which generates X-rays to irradiate an object in a compressed state, an X-ray detector which detects X-rays which propagate through the object, a controller which performs a first main shot which irradiates the object by using X-rays at a fixed position and a second main shot which irradiates the object by using X-rays at different positions, and an image processor which forms a two-dimensional final image by removing a lesion region having an unclear boundary from each of a plurality of two-dimensional images which are obtained as a result of the second main shot and substituting a lesion region of a single two-dimensional image which is obtained as a result of the first main shot into an area which corresponds to the removed lesion region.

BRIEF DESCRIPTION OF THE DRAWINGS

The above and/or other aspects will become apparent and more readily appreciated from the following description of exemplary embodiments, taken in conjunction with the accompanying drawings of which:

FIGS. 6A and 6B are block diagrams of an image processor illustrated in FIG. 5;

DETAILED DESCRIPTION

Figure 1:
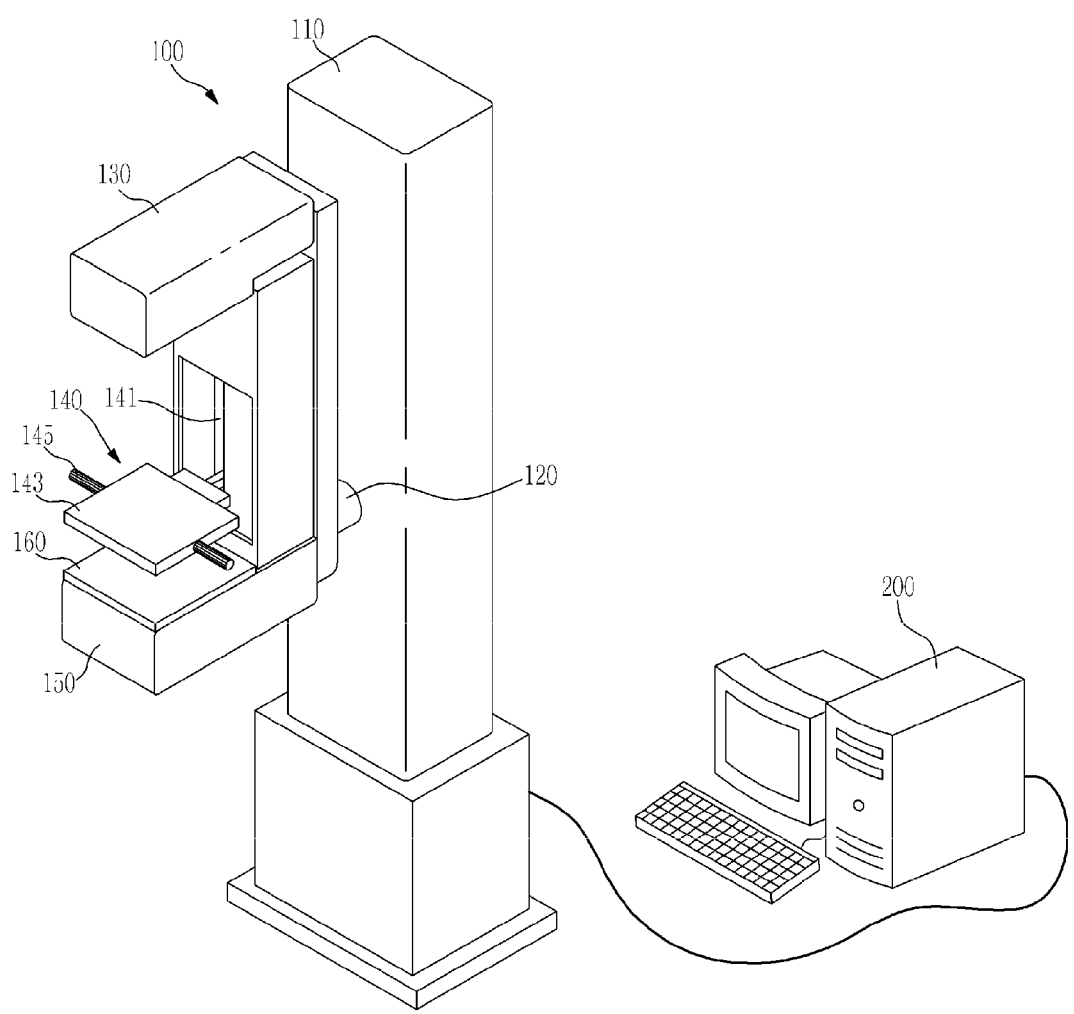
FIG. 1 is a perspective view of an X-ray imaging apparatus, according to an exemplary embodiment.

Reference will now be made in detail to exemplary embodiments, examples of which are illustrated in the accompanying drawings. However, the present inventive concept may be embodied in many different forms and should not be construed as being limited to the exemplary embodiments set forth herein. Rather, these exemplary embodiments are provided so that the present disclosure will be thorough and complete, and will fully convey the scope of the present inventive concept to those skilled in the art, and the spirit and scope of the present inventive concept should be defined by the appended claims.

Hereinafter, exemplary embodiments of an X-ray imaging method and apparatus will be described in detail with reference to the accompanying drawings. In the drawings, like reference numerals refer to like elements.

First, an X-ray imaging apparatus according to an exemplary embodiment will be described with reference to FIGS. 1 through 5.

Figure 2:
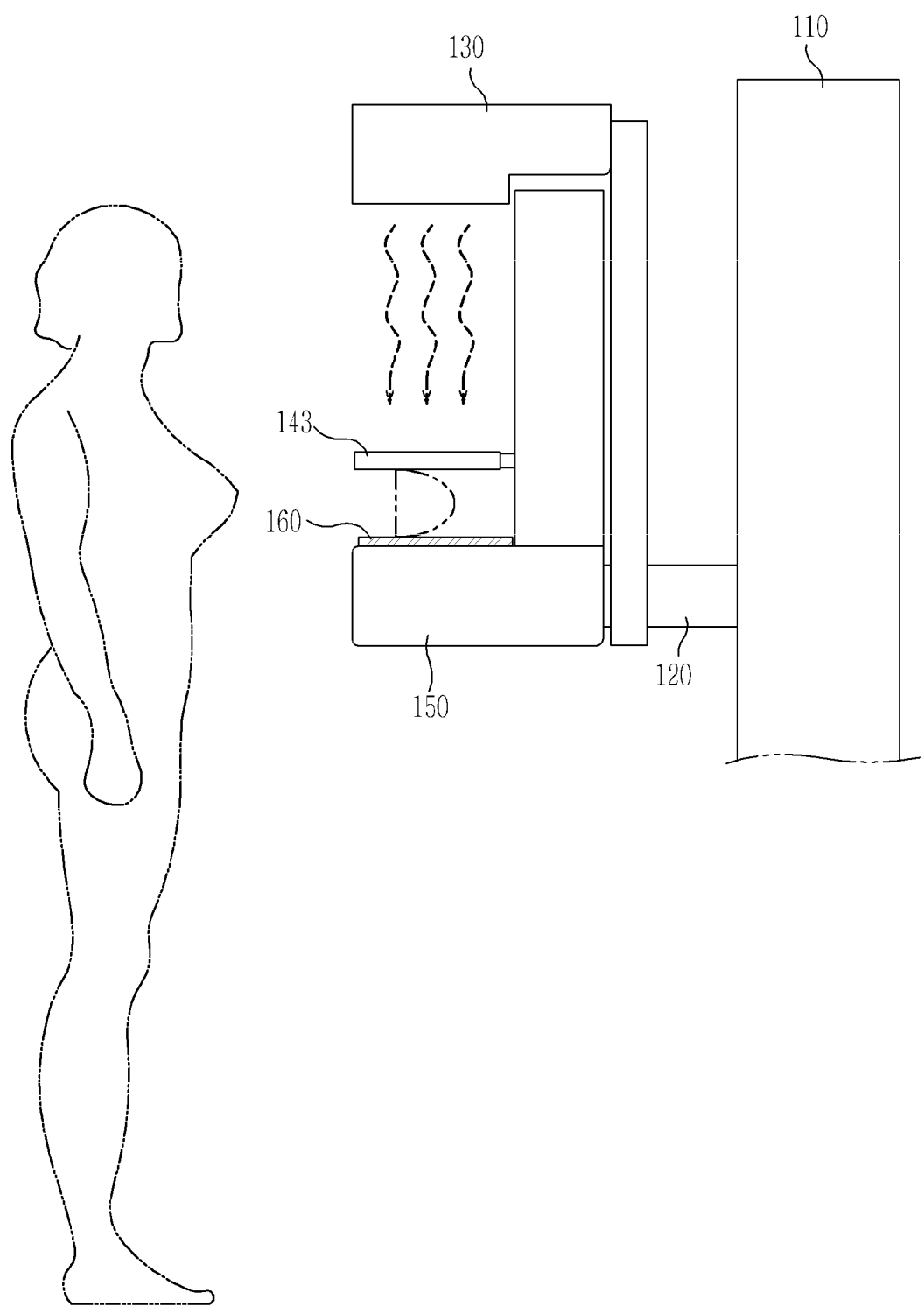
FIG. 2 is a side view of the X-ray imaging apparatus illustrated in FIG. 1.
Figure 3:
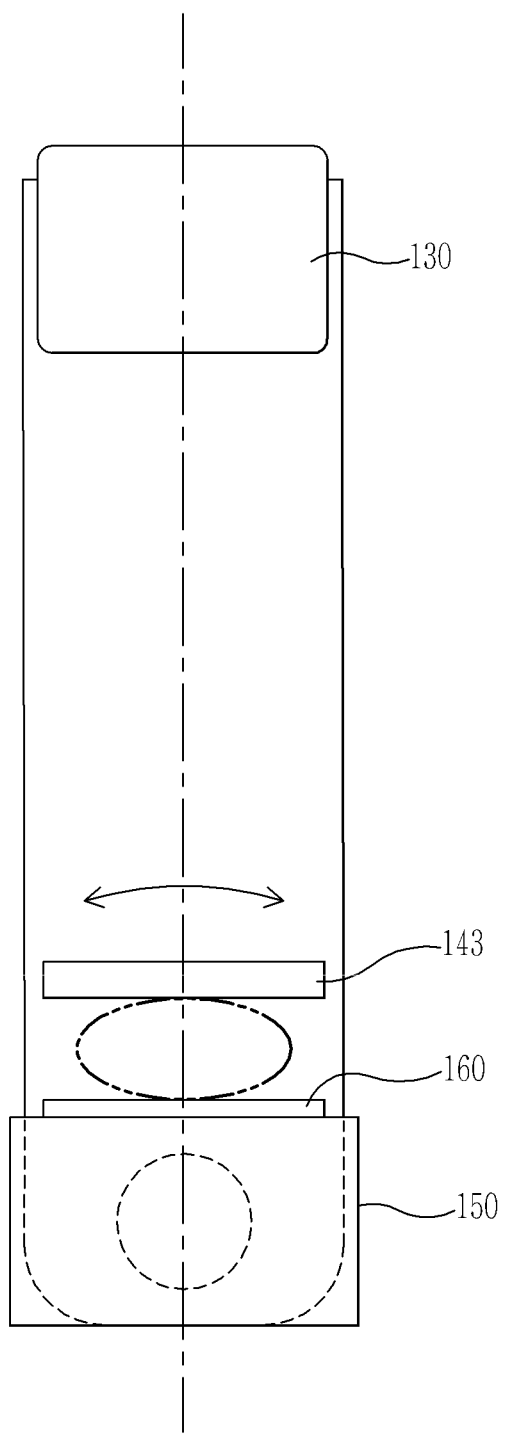
FIG. 3 is a view which illustrates radiography of an object in a state in which an arm of the X-ray imaging apparatus of FIG. 1 is fixed.
Figure 4:
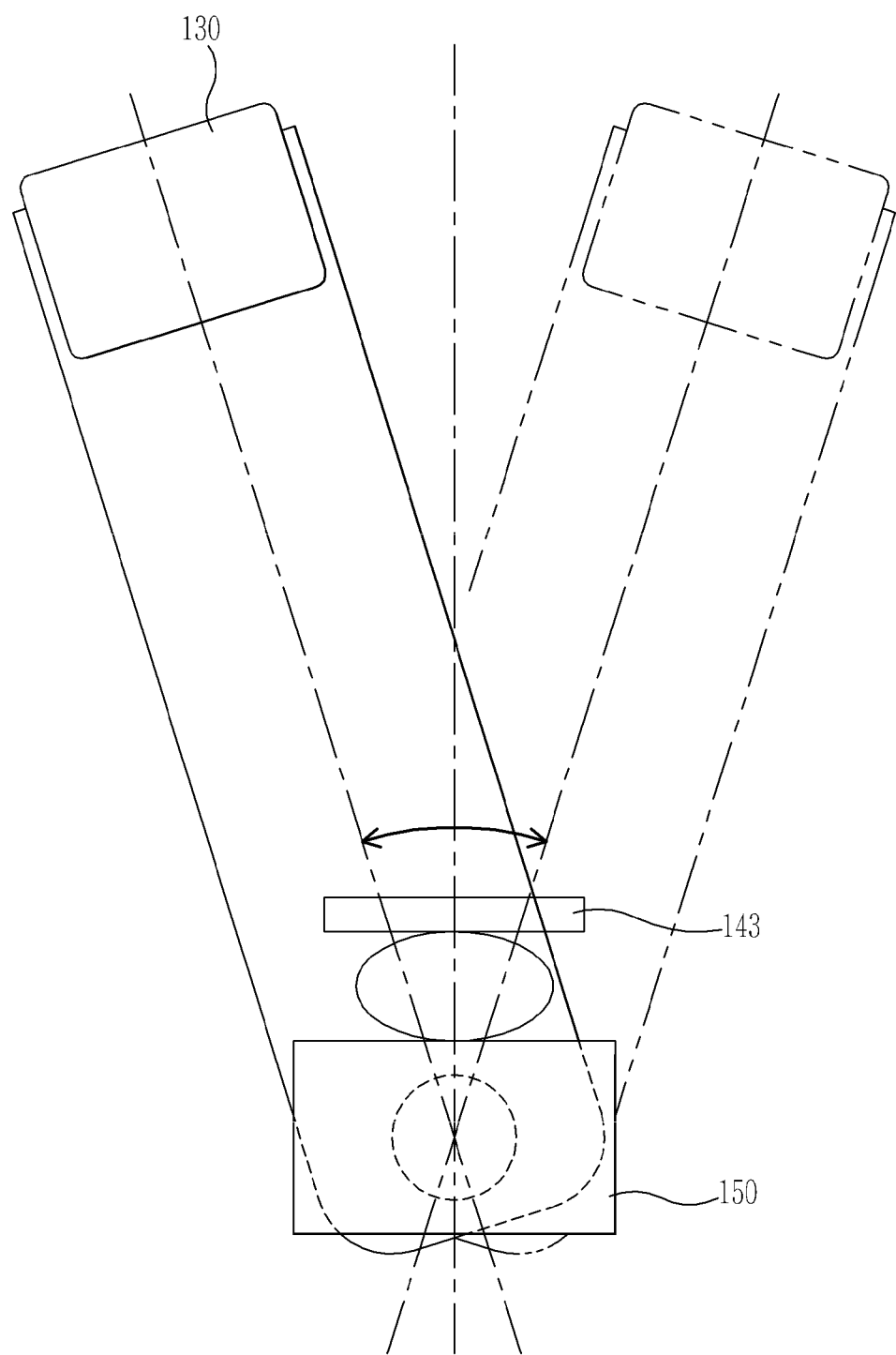
FIG. 4 is a view which illustrates a process for performing radiography on an object by rotating the arm of the X-ray imaging apparatus of FIG. 1.

FIG. 1 is a perspective view of an X-ray imaging apparatus, according to an exemplary embodiment. FIG. 2 is a side view of the X-ray imaging apparatus illustrated in FIG. 1. FIG. 3 is a view which illustrates radiography of an object in a state in which an arm 130 of the X-ray imaging apparatus of FIG. 1 is fixed. FIG. 4 is a view which illustrates a process for performing radiography on an object by rotating the arm 130 of the X-ray imaging apparatus of FIG. 1.

Referring to FIGS. 1, 2, 3, and 4, the X-ray imaging apparatus may include a gantry 100 and an operator workstation 200.

The gantry 100 may perform X-ray imaging of an object (e.g., a breast) in order to form an X-ray image, and then transmit the X-ray image to the operator workstation 200. The gantry 100 may include a main body 110 and the arm 130.

A rotating shaft 120 may be fixedly installed at the main body 110. The main body 110 may include any one or more of various kinds of electronic components which may be used to generate X-rays, any one or more of various kinds of electronic products which may be used to detect X-rays which propagate through an object in order to form an X-ray image, and cables which may be used to connect the electronic components to the electronic products.

The arm 130 may rotate about the rotating shaft 120, which is fixed at the main body 110. The arm 130 may irradiate the object by using X-rays at least once at a fixed position, or may irradiate the object by using X-rays a plurality of times at different positions. When the arm 130 irradiates the object with X-rays at different positions, movement of the arm 130 and X-ray irradiation may be simultaneously performed or alternatingly performed.

In the following descriptions, an irradiation of a compressed object with X-rays is referred to as a "shot." The term "shot," as used herein, may be classified into a pre-shot and a main shot. In this regard, the pre-shot is a shot which is generally performed prior to the main shot and refers to a shot which is performed in order to determine or confirm tissue characteristics of the object and to set one or more radiographic conditions which relate to the main shot based on the confirmed tissue characteristics. The main shot refers to a shot which is performed in accordance with the radiographic conditions set by the pre-shot.

The main shot may be classified at least into a first main shot and a second main shot. As illustrated in FIG. 3, the first main shot refers to an irradiation of an object with X-rays at least once at a fixed position. As illustrated in FIG. 4, the second main shot refers to a respective irradiation of an object with X-rays at different positions.

Figure 5:
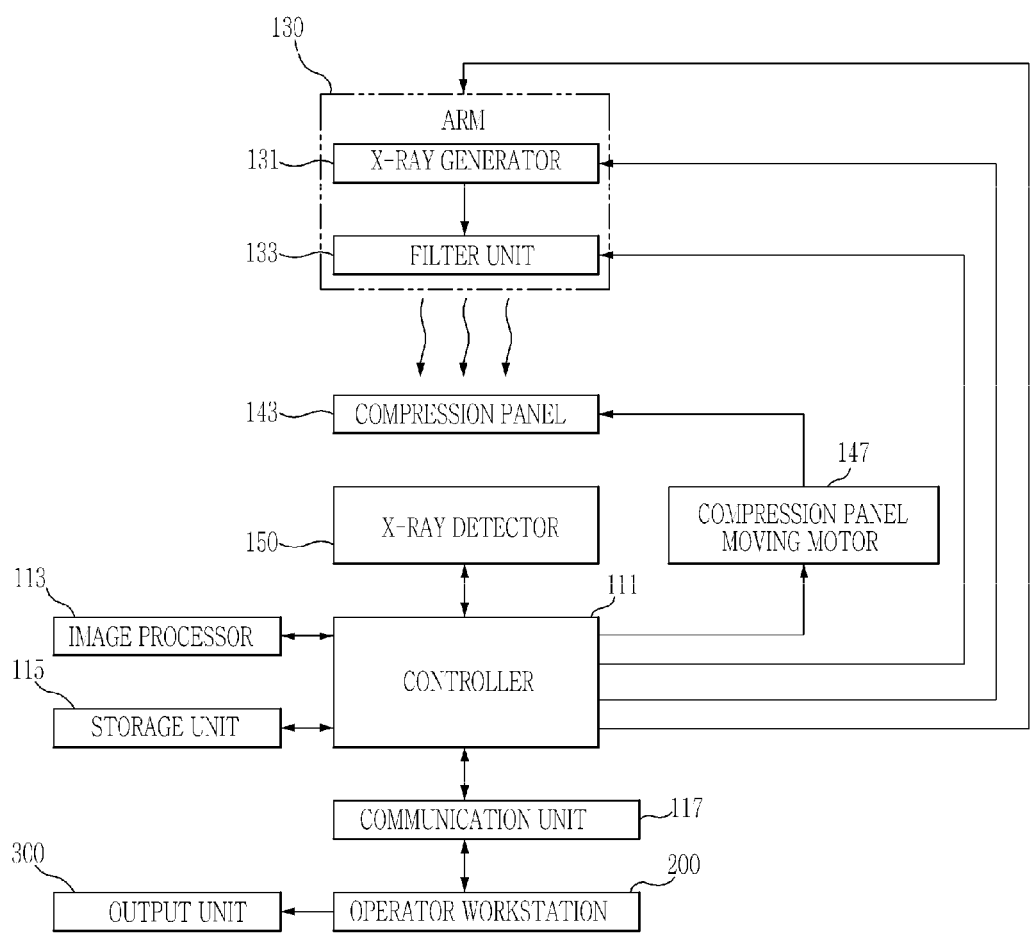
FIG. 5 is a block diagram of the X-ray imaging apparatus, according to an exemplary embodiment.

The arm 130 may include an X-ray generator 131 (see FIG. 5) and a filter unit 133 (see FIG. 5).

The X-ray generator 131 may irradiate the object with X-rays. Hereinafter, X-rays will be briefly described.

X-rays are generated by passing a tube current through a cathode (i.e., a filament) which is arranged in a vacuum X-ray tube and applying a tube voltage between the cathode (filament) and an anode (i.e., a target). In particular, when the tube current flows in the cathode (filament), the cathode (filament) is heated and electrons are released from the heated cathode (filament). The electrons released from the cathode (filament) are accelerated by the tube voltage, and the anode (target) is bombarded with the accelerated electrons in order to generate X-rays. In this regard, the tube voltage and the tube current may vary based on X-ray imaging apparatuses.

A tube voltage affects the amount and energy (which is a determinant of transmittance) of X-rays which are generated by an X-ray tube. As the tube voltage increases, a peak of a corresponding generated X-ray spectrum increases, and the X-ray spectrum shifts towards a higher energy. This phenomenon indicates that as the tube voltage increases, the number of photons generated by the X-ray tube increases, and overall energy of the photons also increases.

Tube current affects the amount of X-rays generated by an X-ray tube. As the tube current increases, a peak of a corresponding X-ray spectrum increases, but the X-ray spectrum does not shift towards either of a lower energy or a higher energy. This phenomenon indicates that as the tube current increases, the number of photons generated by the X-ray tube increases.

In addition, X-rays may vary based on materials constituting the anode (a target). For example, when the anode (a target) is formed of tungsten and the tube voltage is 42 kVp, an X-ray spectrum of X-rays generated from the anode has a peak which is approximately equal to 24 keV and is expressible as a smooth curve with rising and falling portions. When the anode is formed of molybdenum and the tube voltage is 42 kVp, an X-ray spectrum of X-rays generated from the anode may be represented as a spike-shaped curve having a peak which is approximately equal to 17 keV.

The X-ray generator 131 may rotate together with the arm 130, based on a rotation of the arm 130. In particular, the arm 130 may rotate by a predetermined angle based on a central line which is perpendicular to the object. In this regard, an angle of leftward or rightward rotation of the X-ray generator 131 based on the central line may be defined as an angle of radiography. The angle of radiography may be determined based on tissue characteristics of the object. In this regard, the tissue characteristics of the object may include, for example, a thickness of a breast and a density of the breast.

The filter unit 133 (see FIG. 5) may include at least one filter. The at least one filter may be replaceable by one or more other filters. In this regard, replacement of the filter may be performed manually or automatically.

When X-rays irradiated by the X-ray generator 131 pass through the filter, the peak of the X-ray spectrum decreases and shifts towards a higher energy. Thus, the filter reduces the number of photons (in particular, low-energy photons) and increases energy of the photons. In this regard, the reduced number of photons and increased an average energy of the photons may vary based on the type of filter being used.

For example, when a filter made of copper (Cu) is used, an X-ray spectrum of X-rays may be represented as a spike-shaped curve which has a peak value which is approximately equal to 10 keV. When a filter made of aluminum (Al) is used, an X-ray spectrum of X-rays may be represented as a curve which has a peak value which is approximately equal to 7 keV and which smoothly falls towards a higher energy.

The arm 130 may be provided at a front side thereof with an X-ray detector 150 which includes a surface upon which to place the object and a compressor 140 which compresses the object placed on the X-ray detector 150.

The compressor 140 may include a compression panel 143 and a compression panel guide unit 141.

The compression panel 143 may move upward and downward along a vertical central line. The compression panel 143 may move downward along the central line in order to compress the object.

In an exemplary embodiment, the compression panel 143 may be moved manually. In particular, the compression panel 143 may be provided at at least one of left and right sides thereof with a compression panel handle 145, and an operator may manipulate the compression panel handle 145 and thereby cause the compression panel 143 to move downward in order to compress the object.

In another exemplary embodiment, the compression panel 143 may be automatically moved. In particular, the compression panel 143 may be automatically moved by using a compression panel moving motor 147 (see FIG. 5).

The compression panel guide unit 141 may guide a movement of the compression panel 143. The compression panel guide unit 141 may include the compression panel moving motor 147 (see FIG. 5) inside thereof in order to cause and/or guide a movement of the compression panel 143.

The X-ray detector 150 may be fixedly installed at the rotating shaft 120 of the arm 130 in order to detect X-rays which propagate through the object. As illustrated in FIG. 3, when the first main shot is performed, a grid 160 may be positioned between the object and the X-ray detector 150. The grid 160 absorbs scattered X-rays from among the X-rays which propagate through the object. In particular, when the object is irradiated with X-rays, the irradiated X-rays are partially absorbed by the object and partially propagate through the object. The X-rays which propagate through the object are partially scattered, the scattered X-rays are removed by the grid 160, and only the X-rays which have linearity are detected by the X-ray detector 150. Unlike the first main shot, as illustrated in FIG. 4, the second main shot may be performed in an absence of the grid 160 between the object and the X-ray detector 150.

The operator workstation 200 may receive the X-ray image from the gantry 100. For this operation, the operator workstation 200 may be connected to the gantry 100 via a network. In this regard, the network may include at least one of a wired network and a wireless network.

In addition, referring also to FIG. 5, the operator workstation 200 may output the X-ray image received from the gantry 100 to an output unit 300. The output unit 300 may include at least one of a printer and a display. The display may include at least one of a cathode ray tube (CRT) and a flat panel display. Examples of types of the flat panel display include a liquid crystal display (LCD), a plasma display panel (PDP), and organic light emitting diodes (OLEDs).

FIG. 5 is a control block diagram of the X-ray imaging apparatus, according to an exemplary embodiment.

The X-ray imaging apparatus may further include a controller 111, an image processor 113, a storage unit 115, and a communication unit 117, in addition to the elements described above with reference to FIGS. 1, 2, 3, and 4.

The controller 111 may connect and control elements which constitute the X-ray imaging apparatus, and may perform automatic exposure control (AEC). The term "AEC" as used herein refers to automatic control of X-ray exposure by setting radiographic conditions based on tissue characteristics of the object. In this regard, the tissue characteristics of the object may include, for example, a thickness of a breast and a density of the breast. Thus, in an exemplary embodiment, the controller 111 is used to determine and/or confirm the thickness and/or the density of the breast in order to perform AEC.

The controller 111 may determine and/or confirm the thickness of a breast by using the following method. In an exemplary embodiment, a sensor (not shown) may sense a position of the compression panel 143, and the controller 111 may determine and/or confirm the thickness of a breast based on values received from the sensor. In another exemplary embodiment, the controller 111 may monitor an operation of the compression panel moving motor 147 and determine and/or confirm the thickness of a breast based on monitoring results. For example, the thickness of a breast may be determined and/or confirmed based on the position (i.e., a rotation angle of a rotor of the motor) of the compression panel moving motor 147.

Further, the controller 111 may determine and/or confirm the density of a breast based on an image histogram of a pre-shot image which is obtained by performing a pre-shot. An image histogram is a graph which shows a brightness distribution of an X-ray image. In particular, the controller 111 obtains the entire area of a breast by integrating a total image histogram of a pre-shot image. Portions of the image histogram which have a luminance that is equal to or greater than a reference value are integrated in order to obtain an area of a parenchyma of the breast. Thereafter, a value obtained by dividing the area of the parenchyma by a total area is multiplied by 100 to obtain the density of the breast.

When the tissue characteristics of the breast are determined and/or confirmed using the above-described method, the controller 111 may search for radiographic conditions which correspond to the confirmed tissue characteristics from among radiographic conditions pre-stored in the storage unit 115. In this regard, the controller 111 may search for radiographic conditions which relate to the first main shot and radiographic conditions which relate to the second main shot. Afterwards, the controller 111 may sequentially perform the first main shot and the second main shot based on the radiographic conditions searched for each main shot.

The storage unit 115 may store algorithms or data which relate to an operation of the X-ray imaging apparatus. For example, the storage unit 115 may store radiographic conditions which relate to performing the pre-shot, the first main shot, and the second main shot. In this regard, the radiographic conditions which relate to the first main shot and the radiographic conditions which relate to the second main shot may be stored as a table based on the tissue characteristics of the breast. The radiographic conditions may include, for example, one or more of the number of times of radiography, a radiographic angle, a radiographic position, a tube voltage, tube current, the type of a material constituting a filter, and the type of a material constituting the anode.

The storage unit 115 that stores data may include a non-volatile memory device, such as a read only memory (ROM), a programmable read only memory (PROM), an erasable programmable read only memory (EPROM), or a flash memory, a volatile memory device such as a random access memory (RAM), or a storage medium such as a hard disk or an optical disc, but is not limited thereto. The storage unit 115 may take any other forms known in the art.

The image processor 113 reads out an electrical signal which is transmitted by the X-ray detector 150 in order to obtain an image signal. Signal processing may be performed on the image signal in order to form an X-ray image.

In particular, when the pre-shot is performed, the image processor 113 may form a pre-shot image as an X-ray image. When the pre-shot image is formed, the image processor 113 may generate an image histogram of the pre-shot image. The image histogram of the pre-shot image is supplied to the controller 111 to be used to confirm the density of a breast.

When the first main shot is performed, the image processor 113 may form a single two-dimensional image as an X-ray image. The single two-dimensional image formed by the first main shot may be an X-ray image which is obtained by radiating X-rays only once in the first main shot, or an X-ray image which is selected from a plurality of X-ray images which are obtained by radiating X-rays several times in the first main shot.

When the second main shot is performed, the image processor 113 may form a plurality of two-dimensional images as an X-ray image. When a lesion is present inside the object, a boundary of a lesion region is generally more distinct in the single two-dimensional image formed by the first main shot than in the plurality of two-dimensional images formed by the second main shot. This is because a higher dose of X-rays is generally used in the first main shot than in the second main shot, and also because the grid 160 is often used in the first main shot but not used in the second main shot.

The image processor 113 may form a two-dimensional final image having relatively low noise in soft tissue images and showing a clear lesion region by using the two-dimensional image which is obtained as a result of the first main shot and the two-dimensional images which are obtained as a result of the second main shot. In this regard, the two-dimensional final image may be formed by using one of a non-iterative reconstruction method or an iterative reconstruction method. Hereinafter, the image processor 113 will be described in greater detail with reference to FIGS. 6A and 6B.

First, the image processor 113 that forms the two-dimensional final image by using a non-iterative reconstruction method will be described with reference to FIG. 6A.

As illustrated in FIG. 6A, the image processor 113 may include an image generation unit 31, an image histogram generation unit 32, an intermediate image generation unit 33, a non-iterative reconstruction image generation unit 34, a virtual image generation unit 36, and a final image generation unit 37. In this context, the term "unit" may refer to a software component or may refer to a hardware component, such as a processor or an integrated circuit, for example, a Field Programmable Gate Array (FPGA) or Application Specific Integrated Circuit (ASIC), which performs a particular function.

The image generation unit 31 may read out an electrical signal which is received from the X-ray detector 150 and process the electrical signal in order to form an X-ray image.

For example, when the pre-shot is performed, the image generation unit 31 may process the electrical signal which is read out from the X-ray detector 150 in order to form a pre-shot image.

When the first main shot is performed, the image generation unit 31 may process the electrical signal which is read out from the X-ray detector 150 in order to form a single two-dimensional image. When a lesion, such as, for example, a microcalcification, is present inside the object, a lesion region which corresponds to the microcalcification is clearly visible in the single two-dimensional image which is obtained by performing the first main shot. As described above, this is because a higher dose of X-rays and the grid 160 are used in the first main shot. The two-dimensional image of the clear lesion region may be supplied to the virtual image generation unit 36, which will be described below.

When the second main shot is performed, the image generation unit 31 may process the electrical signal which is read out from the X-ray detector 150 in order to form a plurality of two-dimensional images. When a lesion, such as, for example, a microcalcification, is present inside a breast, the corresponding lesion regions are unclear in the plurality of two-dimensional images. As described above, this is because during the second main shot, the X-ray generator 131 irradiates the object with a relatively low dose of X-rays while moving, and thus the X-rays which are irradiated from the X-ray generator 131 are partially scattered. Thus, small lesion regions, such as microcalcifications, are unclear in the two-dimensional images which are obtained by performing the second main shot.

The image histogram generator 32 may generate an image histogram of a pre-shot image. The image histogram may be supplied to the controller 111 to be used to determine and/or confirm the density of the breast or other object.

The intermediate image generation unit 33 receives the two-dimensional images which are obtained as a result of the second main shot, each showing an unclear lesion region, from the image generation unit 31. The intermediate image generation unit 33 removes the lesion region from each of the two-dimensional images in order to form a plurality of two-dimensional intermediate images. The intermediate images may be generated by using any one or more of various methods.

As an example, the two-dimensional intermediate images in which lesion regions are unclear may be passed through a high pass filter (HPF) and, as a result, only lesion regions such as microcalcifications remain. Thus, a difference between the two-dimensional images before and after passing through the HPF may be calculated in order to form two-dimensional intermediate images from which the lesion regions are removed.

As another example, a lesion region such as microcalcification may be detected from each two-dimensional image by applying a computer-aided diagnosis (CAD), and a difference between the two-dimensional images before and after the application of CAD may be calculated in order to form two-dimensional intermediate images from each of which the lesion region is removed.

The non-iterative reconstruction image generation unit 34 may include a first reconstruction image generation unit 34a and a second reconstruction image generation unit 34b.

The first reconstruction image generation unit 34a may receive the plurality of two-dimensional images from the image generation unit 31 in order to form a three-dimensional reconstruction image. In this regard, the three-dimensional reconstruction image refers to a three-dimensional image which is reconstructed from two-dimensional X-ray images of an actual object, in order to be viewed in a manner which is similar to viewing the actual object. The first reconstruction image generation unit 34a may generate a three-dimensional reconstruction image which includes a lesion region by using a non-iterative reconstruction method. The non-iterative reconstruction method refers to a formation of a three-dimensional reconstruction image by applying, to a plurality of two-dimensional images, an inverse function of a transform function which is used for two-dimensional modeling of a three-dimensional object. The non-iterative reconstruction method may include, for example, a filtered back projection method.

The two-dimensional images which are received from the image processor 31 are obtained by irradiating the object with a low dose of X-rays while moving the X-ray generator 131. Thus, a lesion region, such as a microcalcification, is poorly visible in each of the two-dimensional images. Accordingly, when the first reconstruction image generation unit 34a forms a three-dimensional reconstruction image by using the two-dimensional images, the lesion region, such as the microcalcification, is poorly visible in the generated three-dimensional reconstruction image. The three-dimensional reconstruction image which is generated by the first reconstruction image generation unit 34a may be transmitted to the operator workstation 200 via the controller 111 and the communication unit 117.

The second reconstruction image generation unit 34b may receive the two-dimensional intermediate images from each of which the lesion region is removed, from the intermediate image generation unit 33, in order to form a three-dimensional reconstruction image from which the lesion region is removed. In this regard, the second reconstruction image generation unit 34b may form the three-dimensional reconstruction image from which the lesion region is removed by using a non-iterative reconstruction method. The generated three-dimensional reconstruction image may be supplied to the virtual image generation unit 36.

The virtual image generation unit 36 may receive the three-dimensional reconstruction image from which the lesion region is removed from the second reconstruction image generation unit 34b. The three-dimensional reconstruction image from which the lesion region is removed may be simulated in order to form a two-dimensional virtual image from which the lesion region is removed. In particular, a three-dimensionally reconstructed object may be virtually irradiated with X-rays in order to obtain the two-dimensional virtual image from which the lesion region is removed. Prior to such a simulation operation, the virtual image generation unit 36 may perform image processing upon the three-dimensional reconstruction image. For example, the three-dimensional reconstruction image may be subjected to image processing for quality improvement of the three-dimensional reconstruction image. When a simulation is performed after such image processing, a two-dimensional virtual image with relatively low noise in soft tissue of a breast may be obtained. However, it may not be necessary to perform image processing upon the three-dimensional reconstruction image, and the image processing operation may be omitted. The two-dimensional virtual image which is formed as a result of the simulation may be supplied to the final image generation unit 37.

The final image generation unit 37 receives the two-dimensional virtual image and the single two-dimensional image which is obtained by performing the first main shot. In addition, the final image generation unit 37 may form a final image in which the lesion region of the single two-dimensional image which is obtained as a result of the first main shot is substituted into an area which corresponds to the area from which the lesion region was removed from the two-dimensional virtual image.

In this regard, the two-dimensional final image may be formed by using any one or more of various methods. As an example, the final image generation unit 37 may combine the two-dimensional image which is obtained as a result of the first main shot with the two-dimensional virtual image in order to form a final image. As another example, the final image generation unit 37 may detect the lesion region from the single two-dimensional image which is obtained as a result of the first main shot, and combine the detected lesion region with an area which corresponds to the removed lesion region from the two-dimensional virtual image in order to form a final image. The two-dimensional final image which is obtained by using the above-described method may be supplied to the controller 111, and the two-dimensional final image supplied to the controller 111 may be transmitted to the operator workstation 200 via the communication unit 117.

Next, the image processor 113 that forms a two-dimensional virtual image by using an iterative reconstruction method will be described with reference to FIG. 6B.

Figure 6B:
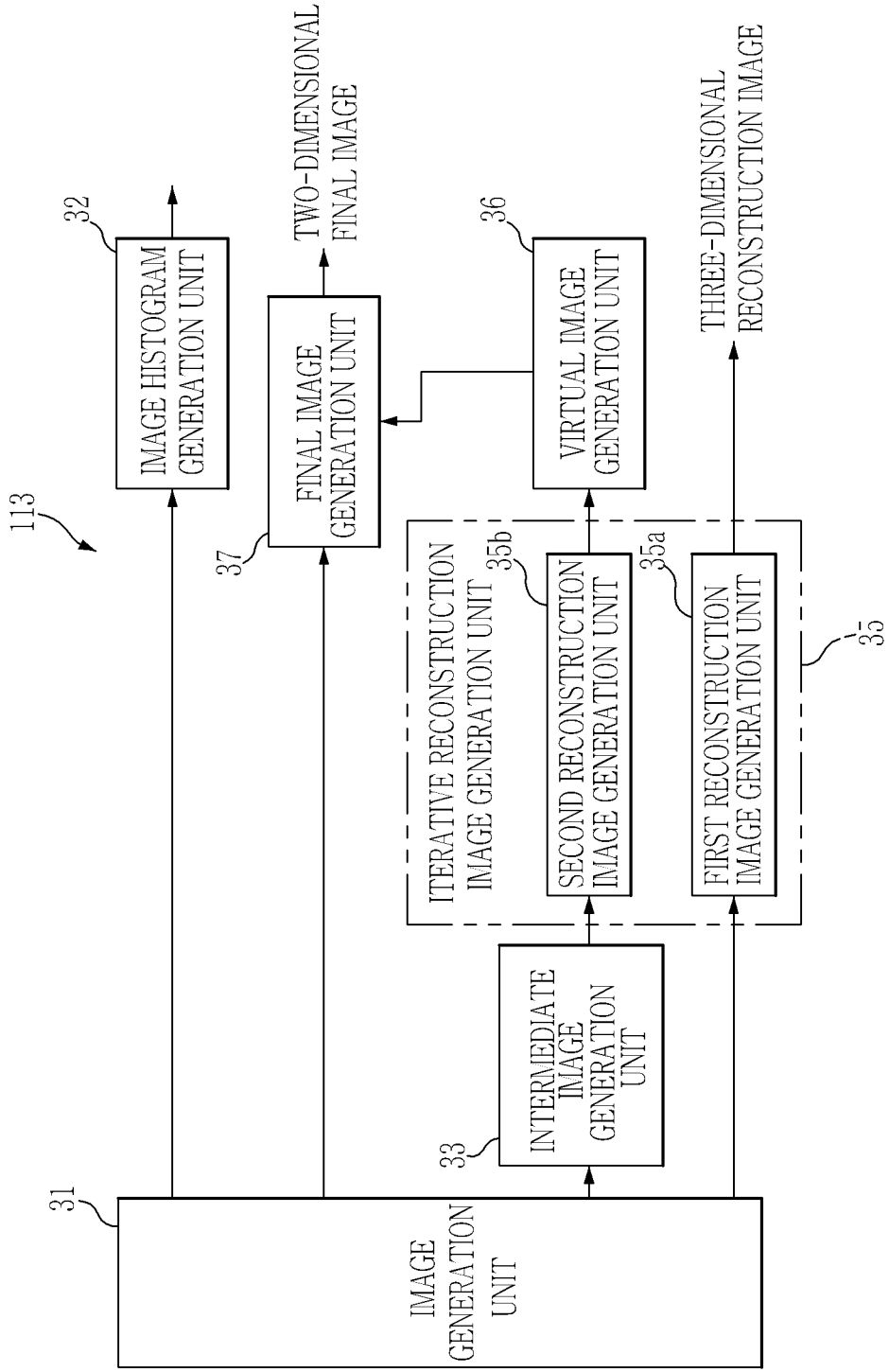

As illustrated in FIG. 6B, the image processor 113 may include an image generation unit 31, an image histogram generator 32, an intermediate image generation unit 33, an iterative reconstruction image generation unit 35, a virtual image generation unit 36, and a final image generation unit 37.

The image generation unit 31, the image histogram generator 32, the intermediate image generation unit 33, the virtual image generation unit 36, and the final image generation unit 37 illustrated in FIG. 6B are the same as those illustrated in FIG. 6A and thus these elements will be described briefly and the iterative reconstruction image generation unit 35 will be focused upon in the following description.

The image generation unit 31 may read out an electrical signal which is received from the X-ray detector 150 and process the electrical signal in order to form an X-ray image.

For example, when the pre-shot is performed, the image generation unit 31 may process the electrical signal which is read out from the X-ray detector 150 in order to form a pre-shot image.

When the first main shot is performed, the image generation unit 31 may process the electrical signal which is read out from the X-ray detector 150 in order to form a single two-dimensional image. When a lesion, such as a microcalcification, is present inside the object, a lesion region which corresponds to the microcalcification is clearly visible in the single two-dimensional image which is obtained by performing the first main shot.

When the second main shot is performed, the image generation unit 31 may process the electrical signal which is read out from the X-ray detector 150 in order to form a plurality of two-dimensional images. In this regard, the corresponding lesion regions are poorly visible in the plurality of two-dimensional images. The two-dimensional images in which lesion regions are poorly visible may be supplied to the intermediate image generation unit 33, which will be described below.

The image histogram generator 32 may generate an image histogram of a pre-shot image. The image histogram may be supplied to the controller 111 to be used to determine and/or confirm a density of a breast.

The intermediate image generation unit 33 may remove the lesion region from each of the two-dimensional images in order to form a plurality of two-dimensional intermediate images.

The iterative reconstruction image generation unit 35 may include a first reconstruction image generation unit 35a and a second reconstruction image generation unit 35b.

The first reconstruction image generation unit 35a may receive the plurality of two-dimensional images from the image generation unit 31 in order to form a three-dimensional reconstruction image. In this regard, the first reconstruction image generation unit 35a may form the three-dimensional reconstruction image by using the iterative reconstruction method. The generated three-dimensional reconstruction image may contain a lesion region, a boundary of which is poorly visible.

In particular, the two-dimensional images received from the image generation unit 31 are obtained by radiation of a low dose of X-rays while moving the X-ray generator 131 during performance of the second shot. Thus, a lesion region, such as a microcalcification, is blurred in each of the two-dimensional images. Accordingly, when the first reconstruction image generation unit 35a forms a three-dimensional reconstruction image by using the two-dimensional images, the three-dimensional reconstruction image contains a blurred lesion region which corresponds to the microcalcification.

The three-dimensional reconstruction image generated by the first reconstruction image generation unit 35a may be supplied to the second reconstruction image generation unit 35b. Alternatively, the three-dimensional reconstruction image may be transmitted to the operator workstation 200 via the controller 111 and the communication unit 117.

The second reconstruction image generation unit 35b may receive the three-dimensional reconstruction image which includes a lesion region from the first reconstruction image generation unit 35a. In addition, the second reconstruction image generation unit 35b may receive the two-dimensional intermediate images, from each of which the lesion region is removed, from the intermediate image generation unit 33. Moreover, the second reconstruction image generation unit 35b may generate a three-dimensional reconstruction image from which the lesion region is removed by using an iterative reconstruction method.

In particular, the second reconstruction image generation unit 35b may set the three-dimensional reconstruction image which includes a lesion region as a default value, and then update the three-dimensional reconstruction image which is set as a default value by using the two-dimensional intermediate images. As a result, the second reconstruction image generation unit 35b may generate a three-dimensional reconstruction image which has a same volume as that of the three-dimensional reconstruction image generated by the first reconstruction image generation unit 35a and from which the lesion region is removed.

As described above, when the iterative reconstruction image generation unit 35 uses an iterative reconstruction method, a corresponding computational load is greater than when a non-iterative reconstruction method is used, whereas overall image quality may be improved.

Referring back to FIG. 5, the communication unit 117 may serve to transmit and receive data to and from the operator workstation 200. The communication unit 117 may include a hardware component which is capable of performing transmitting and receiving operations, such as, for example, a transmitter/receiver, a transceiver, and/or a tuner. For example, the communication unit 117 may transmit the three-dimensional reconstruction image which is generated by the first reconstruction image generation unit 34a or 35a and the two-dimensional final image which is generated by the final image generation unit 37 to the operator workstation 200. In addition, the communication unit 117 may receive a control signal which is related to operation of the gantry 100 from the operator workstation 200.

The operator workstation 200 may output the three-dimensional reconstruction image and the two-dimensional final image which are received from the gantry 100 via the output unit 300. For example, when the output unit 300 is a display, the display may display the three-dimensional reconstruction image and the two-dimensional final image in parallel. In this regard, the two-dimensional final image has improved image quality for soft tissues of breasts and a lesion region, such as a microcalcification, is clearly visible therein, and thus a presence of the microcalcification and/or a presence of a lump may be easily confirmed. In addition, the three-dimensional reconstruction image is displayed together with the two-dimensional final image, and thus an operator may utilize the two images in executing a diagnosis by performing a comparison therebetween.

Figure 7:
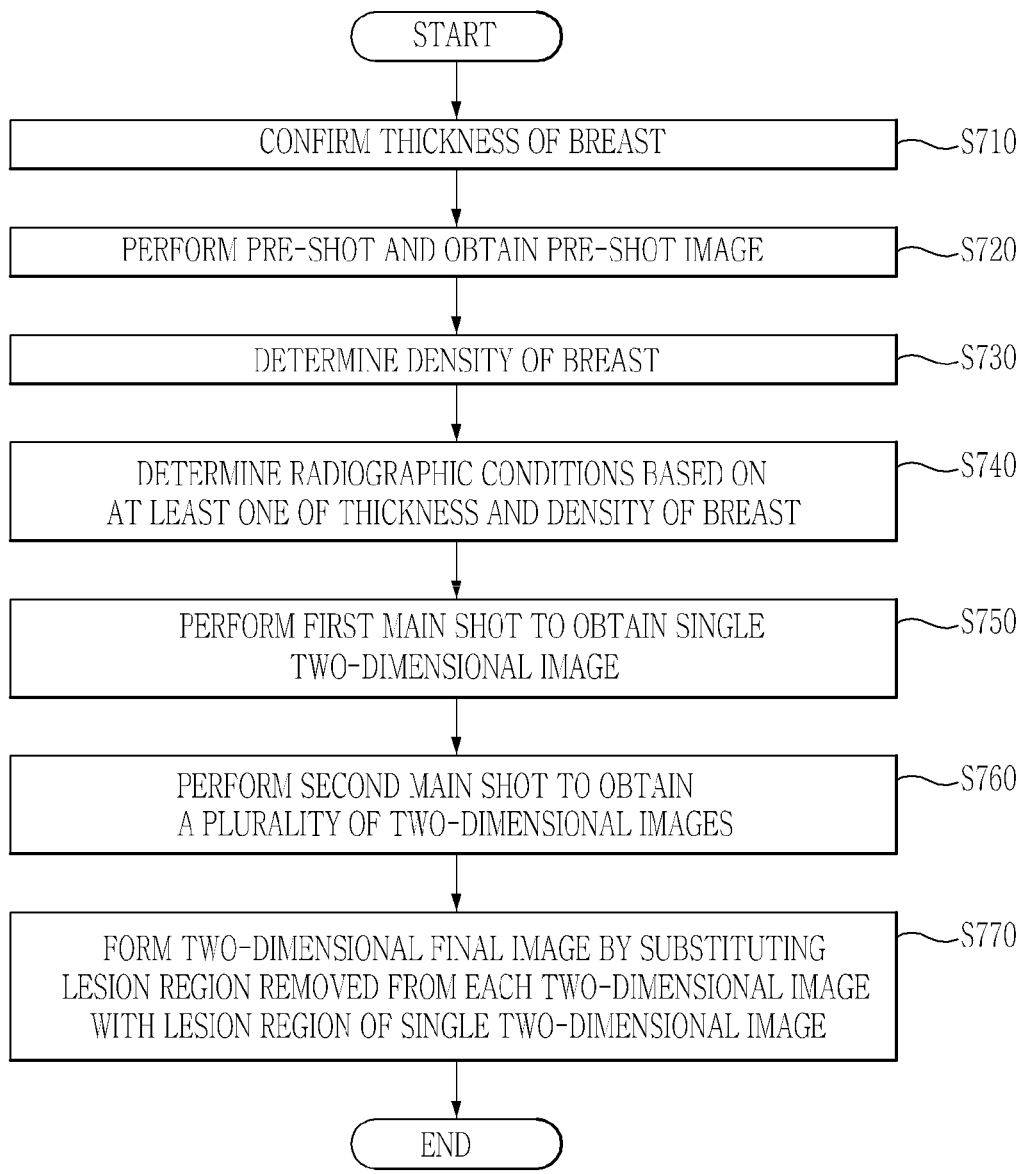
FIG. 7 is a flowchart which illustrates an X-ray imaging method, according to an exemplary embodiment.

Next, an X-ray imaging method according to an exemplary embodiment will be described with reference to FIG. 7.

When a breast is compressed in a state in which the breast of a patient is placed on the X-ray detector 150 by moving the compression panel 143 downward, in operation S710, the controller 111 determines and/or confirms the thickness of the breast. The thickness of the breast may be determined and/or confirmed based on values received from a sensor which senses a position of the compression panel 143, or based on monitoring results of operation of the compression panel moving motor 147.

When the thickness of the breast is confirmed, the X-ray generator 131 radiates X-rays in order to perform a pre-shot. Subsequently, in operation S720, the image processor 113 may read out an electrical signal of the X-ray detector 150 in order to obtain an image signal and perform signal processing upon the image signal in order to generate a pre-shot image. In addition, the image processor 113 may form an image histogram of the pre-shot image to be supplied to the controller 111.

In operation S730, the controller 111 may determine and/or confirm the density of the breast based on the image histogram of the pre-shot image which is received from the image processor 113.

Subsequently, in operation S740, the controller 111 may automatically determine one or more radiographic conditions which relate to performing a main shot, based on at least one of the thickness and the density of the breast. In this regard, the controller 111 may determine one or more radiographic conditions which relate to a first main shot and one or more radiographic conditions which relate to a second main shot. The radiographic conditions may include, for example, at least one of the number of times of radiography, a radiographic angle, a radiographic position, a tube voltage, tube current, the type of a material constituting a filter, and the type of a material constituting the anode.

Thereafter, the X-ray generator 131 irradiates the breast with X-rays based on the determined radiographic conditions which relate to a first main shot in order to perform the first main shot. The first main shot may be performed in a state in which the grid 160 is positioned between the breast and the X-ray detector 150. When the first main shot is performed in operation S750, the image processor 113 may read out the electrical signal of the X-ray detector 150 in order to obtain an image signal, and perform signal processing upon the image signal in order to generate a single two-dimensional image.

Afterwards, the X-ray generator 131 irradiates the breast with X-rays based on the radiographic conditions which relate to a second main shot in order to perform the second main shot. In particular, the breast is irradiated with X-rays repeatedly, based on the number of predetermined times of radiography, while the X-ray detector 150 is moved at a uniform angular speed with respect to the breast in order to perform the second main shot. The second main shot may be performed in the absence of the grid 160 between the breast and the X-ray detector 150. When the second main shot is performed in operation S760, the image processor 113 may read out the electrical signal of the X-ray detector 150 in order to obtain an image signal and then perform signal processing upon the image signal in order to generate a plurality of two-dimensional images.

Figure 8:
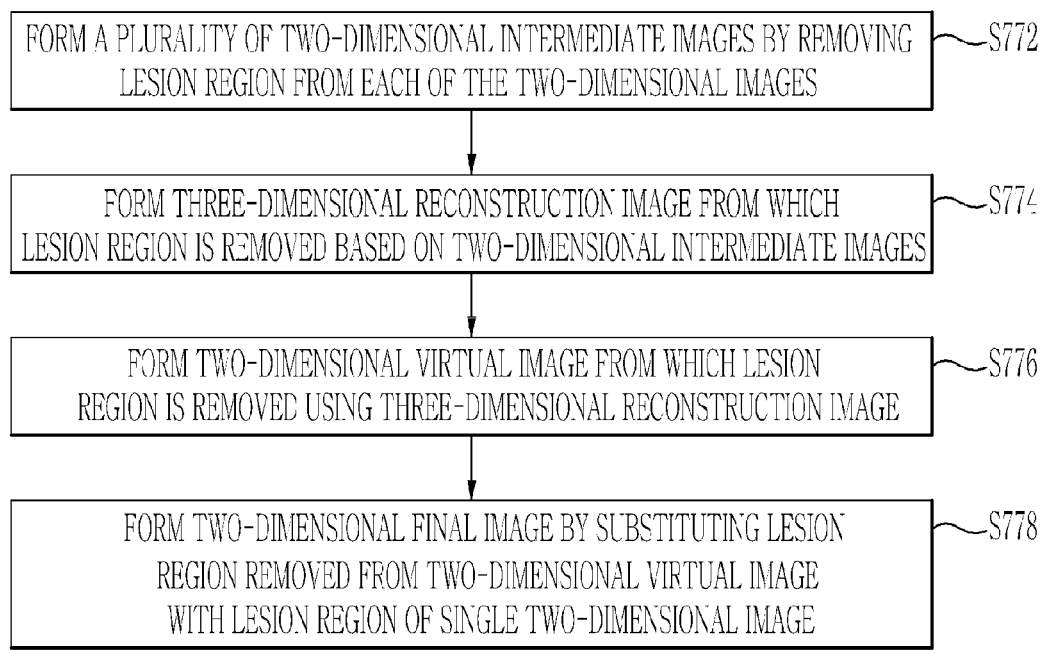
FIG. 8 is a flowchart which illustrates operation S770 as illustrated in FIG. 7.

Then, in operation S770, the image processor 113 may remove a lesion region having an unclear boundary from each of the two-dimensional images which are obtained as a result of the second main shot, and substitute a lesion region of the single two-dimensional image which is obtained as a result of the first main shot into an area which corresponds to the removed lesion region, in order to generate a two-dimensional final image. The two-dimensional final image may be generated by using one of a non-iterative reconstruction method or an iterative construction method. A method for forming a two-dimensional final image by using the non-iterative reconstruction method may be the same as illustrated in FIG. 8.

In particular, in operation S772, the image processor 113 removes the lesion region from each two-dimensional image which is obtained as a result of the second main shot in order to form a plurality of two-dimensional intermediate images.

Next, in operation S774, the image processor 113 forms a three-dimensional reconstruction image from which the lesion region is removed, based on the two-dimensional intermediate images. In this manner, a two-dimensional breast image is three-dimensionally reconstructed. In this regard, the image processor 113 may generate the three-dimensional reconstruction image from which the lesion region is removed by using a non-iterative reconstruction method.

Subsequently, in operation S776, the image processor 113 may simulate the three-dimensional reconstruction image from which the lesion region is removed in order to generate a two-dimensional virtual image from which the lesion region is removed. In particular, the image processor 113 virtually irradiates a three-dimensional reconstruction breast image with X-rays in order to generate a two-dimensional virtual image.

Next, in operation S778, the image processor 113 may substitute the lesion region of the single two-dimensional image which is obtained as a result of the first main shot into an area which corresponds to the removed lesion region in the two-dimensional virtual image in order to generate a two-dimensional final image. For example, the two-dimensional virtual image and the single two-dimensional image which is obtained by performing the first main shot may be simply combined in order to form a two-dimensional final image. Alternatively, the lesion region may be detected from the two-dimensional image which is obtained by performing the first main shot, and the detected lesion region may be combined with the two-dimensional virtual image in order to generate a two-dimensional final image.

Figure 9:
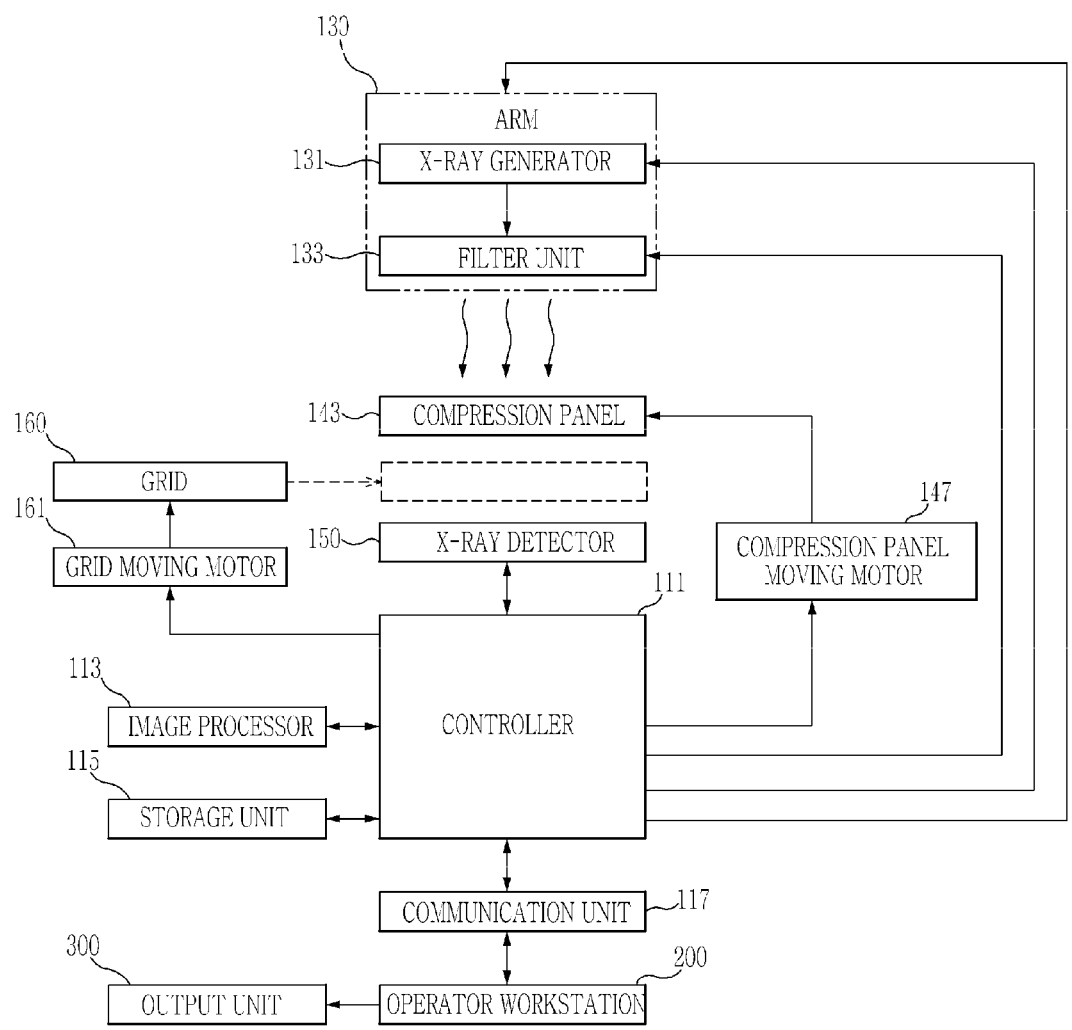
FIG. 9 is a block diagram of an X-ray imaging apparatus, according to another exemplary embodiment.

The X-ray imaging apparatus and method according to exemplary embodiments have been described. Although manual positioning of the grid 160 by an operator is described above with respect to the above-described exemplary embodiment, the grid 160 may be automatically moved. In this case, the X-ray imaging apparatus may further include a grid moving motor 161 which causes the grid 160 to move automatically, as illustrated in FIG. 9.

As is apparent from the above description, an X-ray image having relatively low noise in soft tissue images of breasts and in which a lesion region, such as a microcalcification region, is clearly visible may be obtained.

Some exemplary embodiments have been shown and described. With respect to some exemplary embodiments described above, the filter unit 133 and the image processor 113 among the elements of the X-ray imaging apparatus may be realized as a module. The term "module" may refer to a software component or a hardware component, such as a Field Programmable Gate Array (FPGA) or Application Specific Integrated Circuit (ASIC), which conducts a particular function. However, the module is limited to software or hardware. The module may be configured as being provided in a storage medium that is available to be addressed, or may be configured to use one or more processors.

Examples of the module may include one or more of the following: object oriented software components, class components and task components, processes, functions, attributes, procedures, subroutines, segments of a program code, drivers, firm wares, microcode, circuit, data, database, data structures, tables, arrays, and variables. The functions provided by the components and the modules may be incorporated into a smaller number of components and modules, or may be divided among additional components and modules. In addition, the components and modules as such may use one or more central processing units (CPUs) in a device.

Some exemplary embodiments can also be embodied as a transitory computer-readable medium or as a non-transitory computer-readable medium which includes computer-readable codes/commands to control at least one component of the above-described exemplary embodiments. The medium may include any medium that can store and/or transmit the computer-readable code.

The computer-readable code may be recorded on the medium and may be transmitted via the Internet, and examples of the medium include read-only memory (ROM), random-access memory (RAM), compact disc (CD)-ROMs, magnetic tapes, floppy disks, optical data storage devices, and carrier waves such as waves used for data transmission via the Internet. The medium may be a non-transitory computer-readable medium. The medium can also be distributed over network coupled computer systems so that the computer-readable code is stored and executed in a distributed fashion. In addition, examples of the component to be processed may include a processor or a computer process. The element to be processed may be distributed and/or included in one device.

While exemplary embodiments have been particularly shown and described, it will be understood by those of ordinary skill in the art that various changes in form and details may be made therein without departing from the spirit and scope of the present inventive concept as defined by the following claims.

What is claimed is:

1. An X-ray imaging method comprising:
    performing a first main shot which irradiates an object in a compressed state by using X-rays at least once in order to obtain a single two-dimensional image;
    performing a second main shot which irradiates the object by using X-rays at different positions in order to obtain a plurality of two-dimensional images; and
    forming a two-dimensional final image by removing a lesion region having an unclear boundary from each of the plurality of two-dimensional images which are obtained by performing the second main shot and substituting a lesion region of the single two-dimensional image into an area which corresponds to the removed lesion region.

2. The X-ray imaging method according to claim 1, further comprising:
    determining a thickness of the object;
    performing a pre-shot which irradiates the object by using X-rays in order to obtain a pre-shot image of the object;
    determining a density of the object by using an image histogram of the pre-shot image; and
    determining at least one radiographic condition which relates to the performing the first main shot and the performing the second main shot based on at least one of the thickness and the density of the object, before the performing the first main shot.

3. The X-ray imaging method according to claim 1, wherein the first main shot is performed in a state in which a grid is installed between an X-ray detector which detects the X-rays and the object.

4. The X-ray imaging method according to claim 1, wherein the second main shot is performed without a grid between an X-ray detector which detects the X-rays and the object.

5. The X-ray imaging method according to claim 1, wherein the first main shot is performed by irradiating the object by using a higher dose of X-rays than a dose of X-rays which is used for performing the second main shot.

6. The X-ray imaging method according to claim 1, wherein the forming comprises:
    forming a plurality of two-dimensional intermediate images by removing a lesion region having an unclear boundary from each of the two-dimensional images which are obtained by performing the second main shot;

using the plurality of two-dimensional intermediate images to form a three-dimensional reconstruction image from which the lesion region is removed;

forming a two-dimensional virtual image from which the lesion region is removed by performing a simulation which virtually irradiates the three-dimensional reconstruction image by using X-rays; and forming the final image by substituting the lesion region of the single two-dimensional image into a corresponding area of the two-dimensional virtual image from which the lesion region is removed.

7. The X-ray imaging method according to claim 6, wherein the forming of the final image comprises combining the two-dimensional virtual image with the single two-dimensional image.

8. The X-ray imaging method according to claim 6, wherein the forming of the final image comprises:

detecting the lesion region from the single two-dimensional image; and combining the detected lesion region with the corresponding area of the two-dimensional virtual image.

9. The X-ray imaging method according to claim 1, wherein the forming comprises:

forming a three-dimensional reconstruction image which includes a lesion region having an unclear boundary by using the plurality of two-dimensional images which are obtained by performing the second main shot;

forming a plurality of two-dimensional intermediate images by removing the lesion region having an unclear boundary from each of the plurality of two-dimensional images which are obtained by performing the second main shot;

forming a three-dimensional reconstruction image from which the lesion region is removed by using the plurality of two-dimensional intermediate images to update the three-dimensional reconstruction image which includes the lesion region;

forming a two-dimensional virtual image from which the lesion region is removed by performing a simulation which virtually irradiates the three-dimensional reconstruction image from which the lesion region is removed by using X-rays; and forming the final image by substituting the lesion region of the single two-dimensional image into a corresponding area of the two-dimensional virtual image from which the lesion region is removed.

10. An X-ray imaging apparatus comprising:

an X-ray generator which generates X-rays to irradiate an object in a compressed state;

an X-ray detector which detects X-rays which propagate through the object;

a controller which performs a first main shot which irradiates the object by using X-rays at least once at a fixed position and a second main shot which irradiates the object by using X-rays at different positions; and an image processor which forms a two-dimensional final image by removing a lesion region having an unclear boundary from each of a plurality of two-dimensional images which are obtained as a result of the second main shot and substituting a lesion region of a single two-dimensional image which is obtained as a result of the first main shot into an area which corresponds to the removed lesion region.

11. The X-ray imaging apparatus according to claim 10, wherein the controller determines a thickness and a density of the object and determines at least one radiographic condition which relates to the controller performing the first main shot and the second main shot based on at least one of the thickness and the density of the object, before the first main shot is performed.

12. The X-ray imaging apparatus according to claim 10, wherein the first main shot is performed in a state in which a grid is installed between the X-ray detector and the object.

13. The X-ray imaging apparatus according to claim 10, wherein the second main shot is performed without a grid between the X-ray detector and the object.

14. The X-ray imaging apparatus according to claim 10, wherein the first main shot is performed by irradiating the object by using a higher dose of X-rays than a dose of X-rays which is used for performing the second main shot.

15. The X-ray imaging apparatus according to claim 10, wherein the image processor comprises:

an intermediate image generator which forms a plurality of two-dimensional intermediate images by removing a lesion region having an unclear boundary from each of the two-dimensional images which are obtained as a result of the second main shot;

a reconstruction image generator which uses the plurality of two-dimensional intermediate images to form a three-dimensional reconstruction image from which the lesion region is removed;

a virtual image generator which forms a two-dimensional virtual image from which the lesion region is removed by performing a simulation which virtually irradiates the three-dimensional reconstruction image by using X-rays; and a final image generator which forms the final image by substituting the lesion region of the single two-dimensional image into a corresponding area of the two-dimensional virtual image from which the lesion region is removed.

16. The X-ray imaging apparatus according to claim 15, wherein the final image generator combines the two-dimensional virtual image with the single two-dimensional image in order to form the final image.

17. The X-ray imaging apparatus according to claim 15, wherein the final image generator forms the final image by detecting the lesion region from the single two-dimensional image, and combining the detected lesion region with the corresponding area of the two-dimensional virtual image.

18. The X-ray imaging apparatus according to claim 10, wherein the image processor comprises:

a first reconstruction image generator which forms a three-dimensional reconstruction image which includes a lesion region having an unclear boundary by using the plurality of two-dimensional images which are obtained as a result of the second main shot;

an intermediate image generator which forms a plurality of two-dimensional intermediate images by removing a lesion region having an unclear boundary from each of the plurality of two-dimensional images which are obtained as a result of the second main shot;

a second reconstruction image generator which forms a three-dimensional reconstruction image from which the lesion region is removed by using the plurality of two-dimensional intermediate images to update the three-dimensional reconstruction image which includes the lesion region;

a virtual image generator which forms a two-dimensional virtual image from which the lesion region is removed by performing a simulation which virtually irradiates the three-dimensional reconstruction image from which the lesion region is removed by using X-rays; and a final image generator which forms the final image by substituting the lesion region of the single two-dimensional image into a corresponding area of the two-dimensional virtual image from which the lesion region is removed.

* * * * *